«12» United States Patent
Beard et al.

(10) Patent No.: US 10,926,859 B2
(45) Date of Patent: Feb. 23, 2021

(54) SMART WINDOW ACTIVATION TO PREVENT LASER DISTURBANCE

(71) Applicant: INTERNATIONAL BUSINESS MACHINES CORPORATION, Armonk, NY (US)

(72) Inventors: Darren R. Beard, Chandlers Ford (GB); Matthew Fawcett, Hull (GB); Perry Harwood, Liskeard (GB); Sanaz Yeganefard, Eastleigh (GB)

(73) Assignee: International Business Machines Corporation, Armonk, NY (US)

( * ) Notice: Subject to any disclaimer, the term of this patent is extended or adjusted under 35 U.S.C. 154(b) by 327 days.

(21) Appl. No.: 15/916,917

(22) Filed: Mar. 9, 2018

(65) Prior Publication Data

US 2019/0276132 A1    Sep. 12, 2019

(51) Int. Cl.
*B64C 1/14* (2006.01)
*E06B 9/40* (2006.01)
(Continued)

(52) U.S. Cl.
CPC .............. *B64C 1/1492* (2013.01); *E06B 9/40* (2013.01); *G02F 1/0102* (2013.01); *G02F 1/157* (2013.01); *B64D 2011/0061* (2013.01)

(58) Field of Classification Search
CPC ... G02F 1/01; G02F 1/167; G02F 1/19; G02F 1/0102; G02F 1/133514; G02F 1/0121;
(Continued)

(56) References Cited

U.S. PATENT DOCUMENTS

2005/0280897 A1   12/2005   Derenski
2008/0048101 A1   2/2008    Romig et al.
(Continued)

FOREIGN PATENT DOCUMENTS

WO   2006073408 A2   7/2006
WO   2014124622 A1   8/2014

OTHER PUBLICATIONS

Wikipedia, "Smart Glass", Printed on Jan. 24, 2018, 10 Pages, https://en.wikipedia.org/wiki/Smart_glass#Micro-blinds.
(Continued)

*Primary Examiner* — Collin X Beatty
*Assistant Examiner* — Grant A Gagnon
(74) *Attorney, Agent, or Firm* — Anthony M. Pallone (57) ABSTRACT

Method, system and apparatus are provided for smart window activation to prevent laser disturbance. The apparatus may include a window formed of smart glass capable of being activated in discrete sections to be impenetrable to laser light and having a smart glass activation system. A sensor arrangement may detect laser light impacting on the window and may provide data as to the position of the impact on the window. A computer-implemented window protection system may receive input regarding detecting a laser beam impacting a window from the sensor arrangement, determine the position of the laser beam impact on the window and determine a section of the window in which the smart glass is to be activated, and control activation of the smart glass in the section of the window to make the section impenetrable to laser light by instructing the smart glass activation system.

18 Claims, 6 Drawing Sheets

(51) Int. Cl.
*G02F 1/157* (2006.01)
*G02F 1/01* (2006.01)
*B64D 11/00* (2006.01)

(58) Field of Classification Search
CPC .... G02F 1/0128; G02F 1/0136; G02F 1/1676; G02F 1/17; G02F 1/1313; G02F 1/1334; G02F 1/1347; G02F 1/15; G02F 1/1681; G02F 1/21; G02F 1/225; G02F 1/2255; G02F 2201/44; G02F 2202/32; G02F 2203/34; G02F 1/0131; G02F 1/0147; G02F 1/03; G02F 1/13306; G02F 1/13318; G02F 1/133377; G02F 1/133553; G02F 1/133603; G02F 1/157; G02F 1/163; G02F 1/218; G02F 1/23; G02F 1/29; G02F 1/292; G02F 1/2955; G02F 1/31; G02F 1/353; G02F 2001/1678; G02F 2001/212; G02F 2201/16; G02F 2203/10; G02F 2203/12; G02F 2203/15; G02F 2203/50; G02F 1/00; G02F 1/0018; G02F 1/0072; G02F 1/009; G02F 1/0107; G02F 1/011; G02F 1/0115; G02F 1/0123; G02F 1/0126; G02F 1/015; G02F 1/025; G02F 1/0327; G02F 1/0356; G02F 1/11; G02F 1/13; G02F 1/1333; G02F 1/133308; G02F 1/13338; G02F 1/133516; G02F 1/133524; G02F 1/1336; G02F 1/133611; G02F 1/133615; G02F 1/133753; G02F 1/1339; G02F 1/13394; G02F 1/13476; G02F 1/13737; G02F 1/1508; G02F 1/15165; G02F 1/153; G02F 1/155; G02F 1/172; G02F 1/33; G02F 1/35; G02F 1/3526; G02F 1/3551; G02F 1/39; G02F 2001/13312; G02F 2001/13324; G02F 2001/133311; G02F 2001/133374; G02F 2001/133345; G02F 2001/133347; G02F 2001/133601; G02F 2001/133613; G02F 2001/133614; G02F 2001/1351; G02F 2001/1502; G02F 2001/1518; G02F 2001/1536; G02F 2001/1635; G02F 2001/213; G02F 2001/291; G02F 2001/294; G02F 2001/3505; G02F 2201/126; G02F 2201/346; G02F 2201/38; G02F 2201/58; G02F 2202/022; G02F 2202/30; G02F 2203/01; G02F 2203/02; G02F 2203/05; G02F 2203/055; G02F 2203/18; G02F 2203/30; G02F 2203/48; G02F 2203/54; G02F 2203/58; G02F 2203/585; G02F 2203/62; G02F 2/00; E06B 9/24; E06B 2009/2464; E06B 2009/2405; E06B 2009/2417; B64C 1/1484; B64C 1/1492
USPC .......................................................... 359/238
See application file for complete search history.

(56) References Cited

U.S. PATENT DOCUMENTS

2013/0161971 A1* 6/2013 Bugno .................. B64C 1/1484
296/97.2
2014/0039730 A1 2/2014 Loubiere

OTHER PUBLICATIONS

Khomami, "Lasers Targeting Planes: What we Know About the Growing Problem: After a Laser Beam Forced a Virgin Flight to Return to Heathrow, We Look at the Impact of Previous Incidents", Feb. 15, 2016, 3 Pages, The Guardian, https://www.theguardian.com/world/2016/feb/15/lasers-targeting-planes-what-know-about-growing-problem, Printed on Feb. 26, 2018.

Gizmodo, "How the Magical Windows in Boeing's 787 Dreamliner Work", Printed on Mar. 9, 2018, 3 Pages, https://gizmodo.com/5829395/how-boeings-magical-787-dreamliner-windows-work.

* cited by examiner

SMART WINDOW ACTIVATION TO PREVENT LASER DISTURBANCE

BACKGROUND

The present invention relates to smart window activation, and more specifically, to smart window activation to prevent laser disturbance.

There are an increasing number of incidences of laser pointers or other laser devices being shone at aircraft by a person on the ground. People have been known to shine laser light at an aircraft cockpit either on purpose or accidentally. This has the danger that the pilot can be dazzled resulting in potentially serious consequences.

Current steps involve action on the ground to prevent the use of laser devices in the vicinity of airports. However, this is not failsafe and additional measures are required for safety of aircraft.

Similar problems arise if a laser light is shone at a passing vehicle as it may dazzle or disturb the sight of the driver.

BRIEF SUMMARY

According to an aspect of the present invention there is provided a computer-implemented method for smart window activation to prevent laser disturbance, including: receiving input regarding detecting a laser beam impacting a window, wherein the window includes smart glass; determining the position of the laser beam impact on the window and determining a section of the window in which the smart glass is to be activated, wherein the section includes the position of the laser beam impact; and controlling activation of the smart glass in the section of the window to make the section impenetrable to laser light.

According to another aspect of the present invention there is provided a system for smart window activation to prevent laser disturbance, including: a processor and a memory configured to provide computer program instructions to the processor to execute the function of components; a laser monitoring component for receiving input regarding detection of a laser beam impacting a window, wherein the window includes smart glass; a position determining component for determining the position of the laser beam impact on the window and determining a section of the window in which the smart glass is to be activated, wherein the section includes the position of the laser beam impact; and a smart glass operation component for controlling activation of the smart glass in the section of the window to make the section impenetrable to laser light.

According to a further aspect of the present invention there is provided an apparatus for smart window activation, including: a window formed of smart glass capable of being activated in discrete sections to be impenetrable to laser light and having a smart glass activation system; a sensor arrangement arranged to detect laser light impacting on the window and to provide data as to the position of the impact on the window; a computer-implemented window protection system for receiving input regarding detecting a laser beam impacting a window from the sensor arrangement, determining the position of the laser beam impact on the window and determining a section of the window in which the smart glass is to be activated, wherein the section includes the position of the laser beam impact, and controlling activation of the smart glass in the section of the window to make the section impenetrable to laser light by instructing the smart glass activation system.

According to a further aspect of the present invention there is provided a computer program product for smart window activation to prevent laser disturbance, the computer program product including a computer readable storage medium having program instructions embodied therewith, the program instructions executable by a processor to cause the processor to: receive input regarding detecting a laser beam impacting a window, wherein the window includes smart glass; determine the position of the laser beam impact on the window and determine a section of the window in which the smart glass is to be activated, wherein the section includes the position of the laser beam impact; and control activation of the smart glass in the section of the window to make the section impenetrable to laser light.

BRIEF DESCRIPTION OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings.

Preferred embodiments of the present invention will now be described, by way of example only, with reference to the following drawings in which.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numbers may be repeated among the figures to indicate corresponding or analogous features.

DETAILED DESCRIPTION

The described method, system and apparatus provide smart window activation to prevent laser disturbance. This is particularly applicable to windows in aircraft and vehicles where a laser beam may disturb the eyesight or concentration of a pilot or driver; however, this may also be applicable in other situations.

Smart windows may be provided by using known forms of smart glass, also known as switchable glass, whose light transmission properties are altered when voltage, light or heat is applied. Smart glass may change from being transparent, allowing light to pass through it, to becoming impenetrable to some or all wavelengths of light.

The described method, system and apparatus are able to detect a position where a laser contacts a window and to respond by changing the opaqueness of a segment of the window including and surrounding the detected position.

Figure 1:
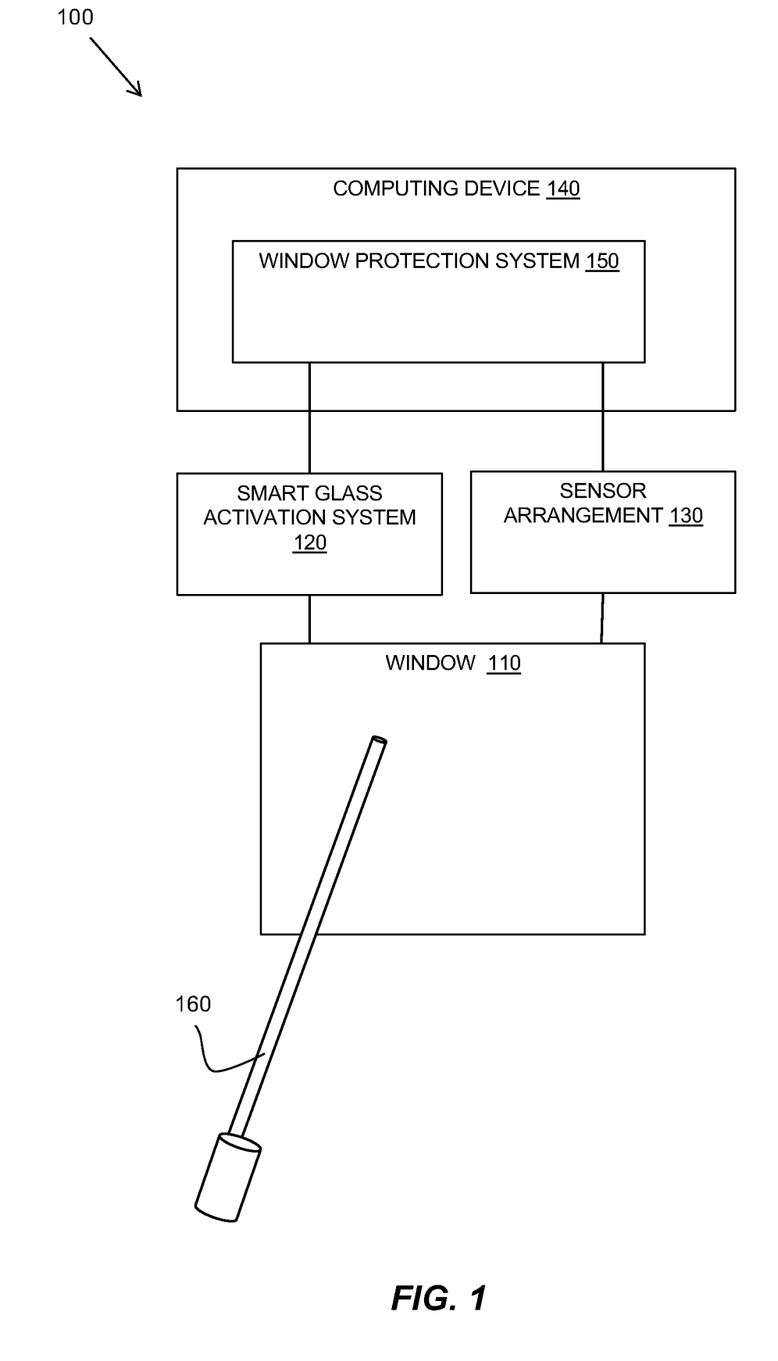
FIG. 1 is a schematic diagram of an example embodiment of an apparatus in accordance with the present invention.

Referring to FIG. 1, a schematic diagram shows an example embodiment of a described apparatus 100 with an illustrated laser beam 160. The apparatus 100 includes a window 110 formed of smart glass and having a smart glass activation system 120 with a sensor arrangement 130 for sensing a laser beam 160 impact on the window 110.

The apparatus 100 also includes a computing device 140 providing a window protection system 150 for receiving input from the sensor arrangement 130 regarding detecting a laser beam (e.g. laser beam 160) impacting the window 110 and controlling the smart glass activation system 120 for activation of the smart glass in a section of the window 110 in which the laser beam 160 impacts to make the section of the window impenetrable to laser light. This may be achieved by the smart window blocking transmission of all light through the activated section of the window.

Figure 2:
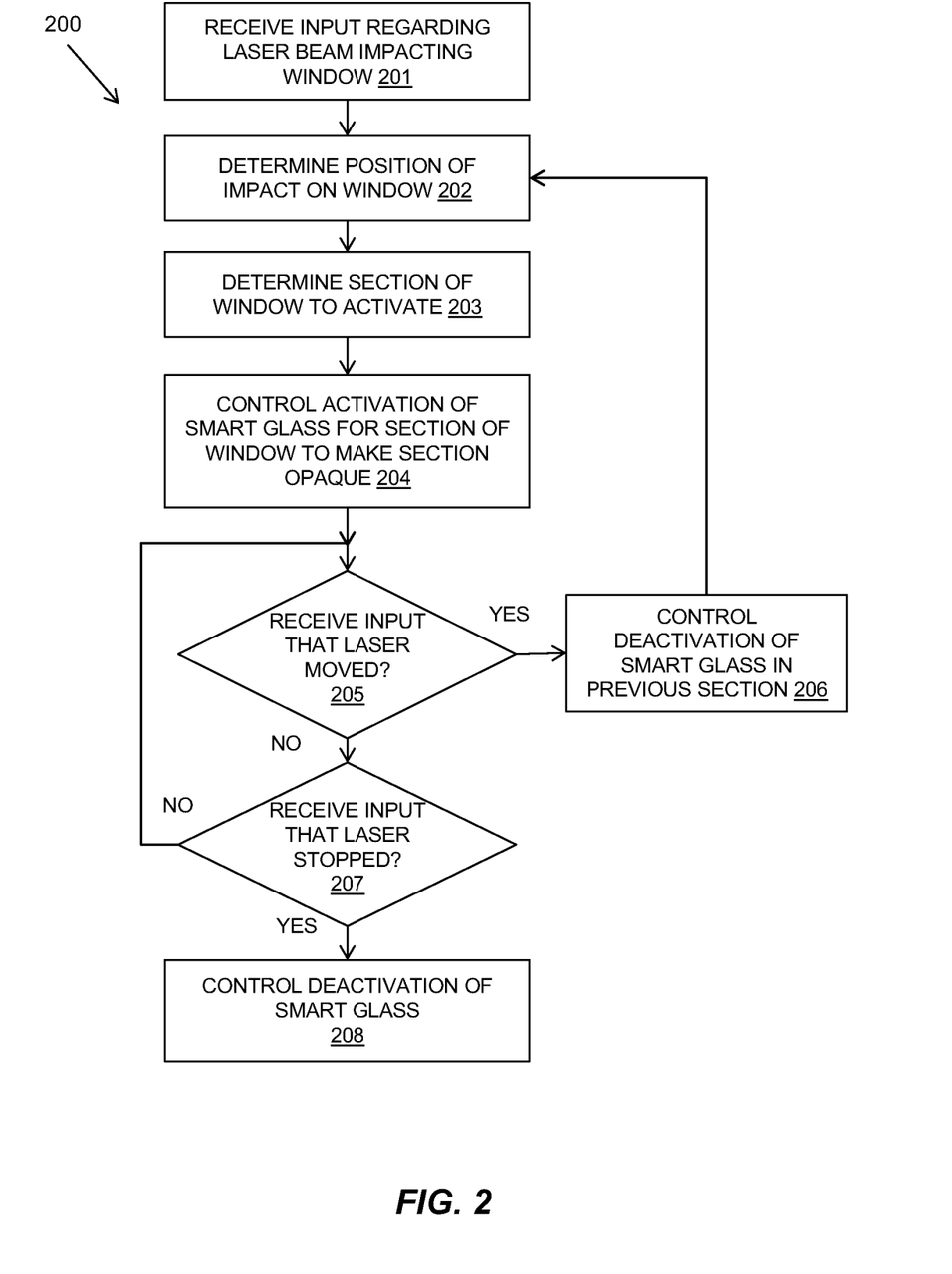
FIG. 2 is a flow diagram of an example embodiment of a method in accordance with the present invention.

Referring to FIG. 2, a flow diagram 200 shows an example embodiment of the described method as carried out by the window protection system 150.

The sensor arrangement 130 described in FIG. 1 may detect a laser beam impact on the window 110 and may provide data regarding the detected laser beam impact to the window protection system 150. The data regarding the detected laser beam impact may include information relating to the position of the impact on the window 110. This may be provided by various methods depending on the form of the sensor arrangement 130 as described further below.

The window protection system 150 may receive (step 201) an input regarding a laser beam impact with the window 110 from the sensor arrangement 130. The position of the laser beam impact on the window may be determined (step 202). A section of the window 110 in which the smart glass is to be activated may also be determined (step 203) where the section includes the position of the detected laser beam impact.

The section of the window may be configured to be an area sufficiently large to prevent disturbance by the laser beam impact to a person behind the window whilst minimizing the restriction to viewing, by the person, through the window. The size and shape of the section may be configured for a particular type and size of window or for a particular situation in which the window is used.

Multiple sections of the window may be predefined as being distinct sections that may be activated and it may be determined which of the predefined sections the position of the impact falls within.

The window protection system 150 may control (step 204) activation of the smart glass in the section of the window to make the section impenetrable to laser light. This activation may take in the order of milliseconds, thereby blocking the laser beams transmission through the window very quickly.

Smart glass may be activated in a few milliseconds, for example, 1 to 10 milliseconds. The activation time may depend on how quickly the laser beam detection can be achieved. This may be estimated an activation in less than 50 milliseconds.

It may be determined if input is received (step 205) from the sensor arrangement 130 that the laser beam impact on the window has moved. If it has moved, the method may control deactivation (step 206) of the smart glass in the previously activated section. The method may repeat the method to determine (step 202) the new position of the laser beam impact on the window and to determine (step 203) a new section of the window 110 in which the smart glass is to be activated where the new section includes the new position of the laser beam impact. The method may control (step 204) activation of the smart glass in the new section of the window to make the new section impenetrable to laser light. In this way, the activated section of the window may track the laser beam as it moves across the window.

In an embodiment, a direction and speed of the movement of the laser beam may be used to anticipate the next position of the laser beam. This may be carried out by the laser position detection system 150 determining the position of the laser beam on the window every few milliseconds. Using this information, the window protection system 150 may determine when the beam is expected to exit the currently activated section of the window and which section of the window will need to be activated so as to continue blocking the beam.

If it is determined (step 205) that the laser beam has not moved, it may be determined (step 207) if input is received from the sensor arrangement 130 that the laser has stopped impacting the window. If it has not stopped, the method may continue to monitor for input that the laser has moved. If input is received that the laser beam has stopped, the method may control (step 208) deactivation of the previously activated smart glass to return the window to its deactivated, fully transparent state.

In an embodiment, the smart glass may be in the form of a micro-blind glass as currently under development at the National Research Council of Canada. Micro-blinds are composed of rolled thin metal blinds on glass and the micro-blinds control the amount of light passing through the glass in response to an applied voltage. The micro-blinds are very small and thus practically invisible to the eye. A metal layer forming the micro-blinds is deposited by magnetron sputtering and patterned by a laser or lithography process. The glass substrate includes a thin layer of a transparent conductive oxide (TCO) and a thin insulator is deposited between the rolled metal layer and the TCO layer for electrical disconnection.

With no applied voltage, the micro-blinds are rolled and let light pass through. When there is a potential difference between the rolled metal layer and the transparent conductive layer, the electric field formed between the two electrodes causes the rolled micro-blinds to stretch out and block light. The micro-blinds have several advantages over other forms of smart glass, including a fast switching speed of several milliseconds, ultra-violet durability, customized appearance and transmission. Such layers forming micro-blinds may be applied to an aircraft or vehicle window.

Figure 3A:
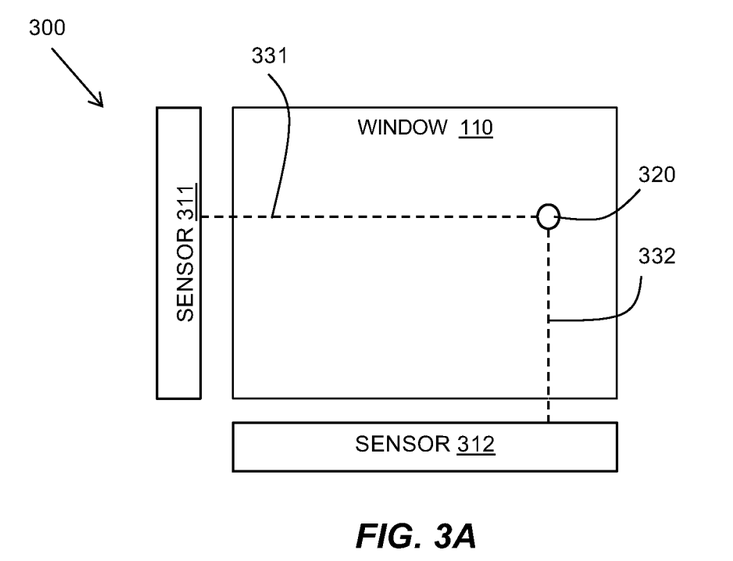
FIGS. 3A and 3B are schematic diagrams of two example embodiments of an apparatus in accordance with the present invention.
Figure 3B:
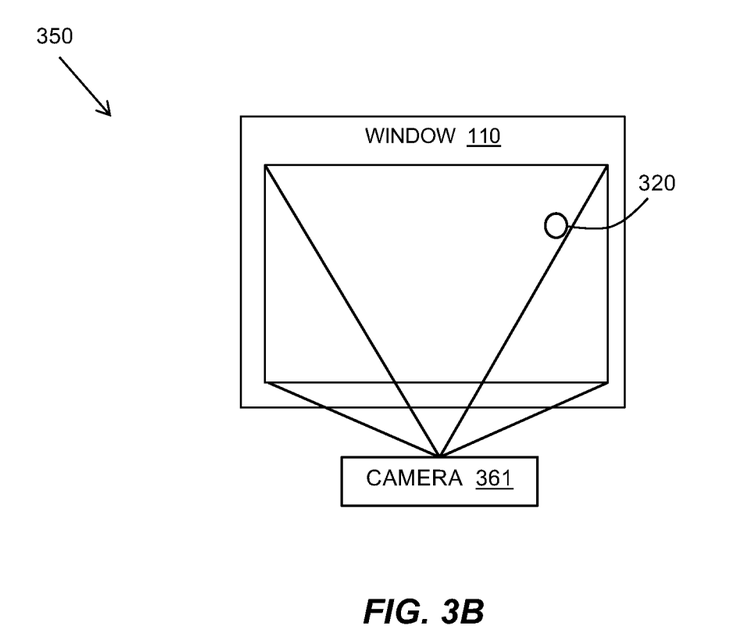

Referring to FIGS. 3A and 3B, schematic diagrams show two embodiments of the described apparatus 300 and 350 by which a laser beam passing through a window 110 may be detected.

In a first embodiment shown in FIG. 3A, light sensors 311, 312 may be positioned along the edges of the glass of the window 110. When the laser passes through the glass, some light is scattered out of the beam and into the glass. By detecting the light (shown by dashed lines 331, 332) along two or more edges of the window 110, the position 320 of the laser beam on the window 110 may be determined. The light sensors 311, 312 may be an array of photo detectors positioned along two or more edges of a window. The light sensors 311, 312 may be scaled up linear array sensors.

In a second embodiment shown in FIG. 3B, a camera 361 may be provided directed at the window 110 which may detect when a laser beam is pointed at the window 110 and may determine the position 320 of the beam on the window 110.

Once the detection has been made, a suitable section of the window 110 may be made impenetrable to the laser light.

This may be achieved by blocking all light transmission in a section of the window 110. In the implementation using micro-blinds, these may be activated by using a small electrical voltage to the section of the window and the response time may be a few milliseconds. This will prevent damage to the eyes of people looking through the window, for example, a pilot trying to control an aircraft.

Figure 4:
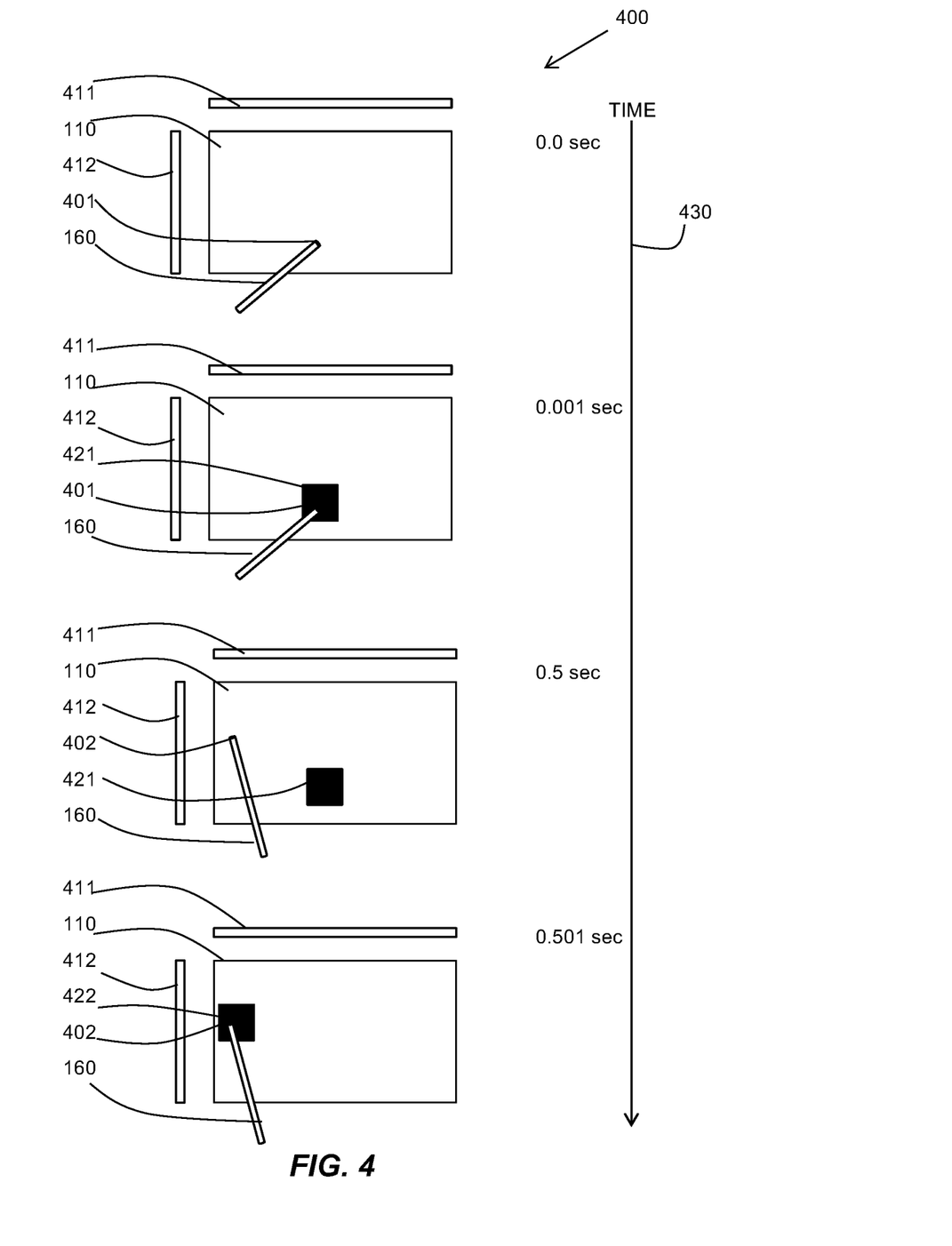
FIG. 4 is a schematic diagram showing an example time series illustrating an example embodiment of the method and apparatus in accordance with the present invention.

Referring to FIG. 4, a time series 400 of schematic diagrams shows an example embodiment of the activation and deactivation of sections of a window 110 in response to impact by a laser beam 160. In this embodiment, the window 110 has sensors 411, 412 that provide data on the position of the laser beam 160 impact. A timeline 430 shows the reaction time between the series.

In a first stage, a laser beam 160 may impact the window 110 at a first position 401 at time 0.0 seconds. In a second stage, the apparatus may react and activate the smart glass at a first section 421 encompassing the first position 401. This may be activated by time 0.001 seconds.

In a third stage, the laser beam 160 may be moved to a second position 402 at time 0.5 seconds. The second position 402 may be outside the activated first section 421. In a fourth stage, at time 0.501 seconds, a new second section 422 may be activated to block the laser beam 160 and the first section 421 may be deactivated.

Figure 5:
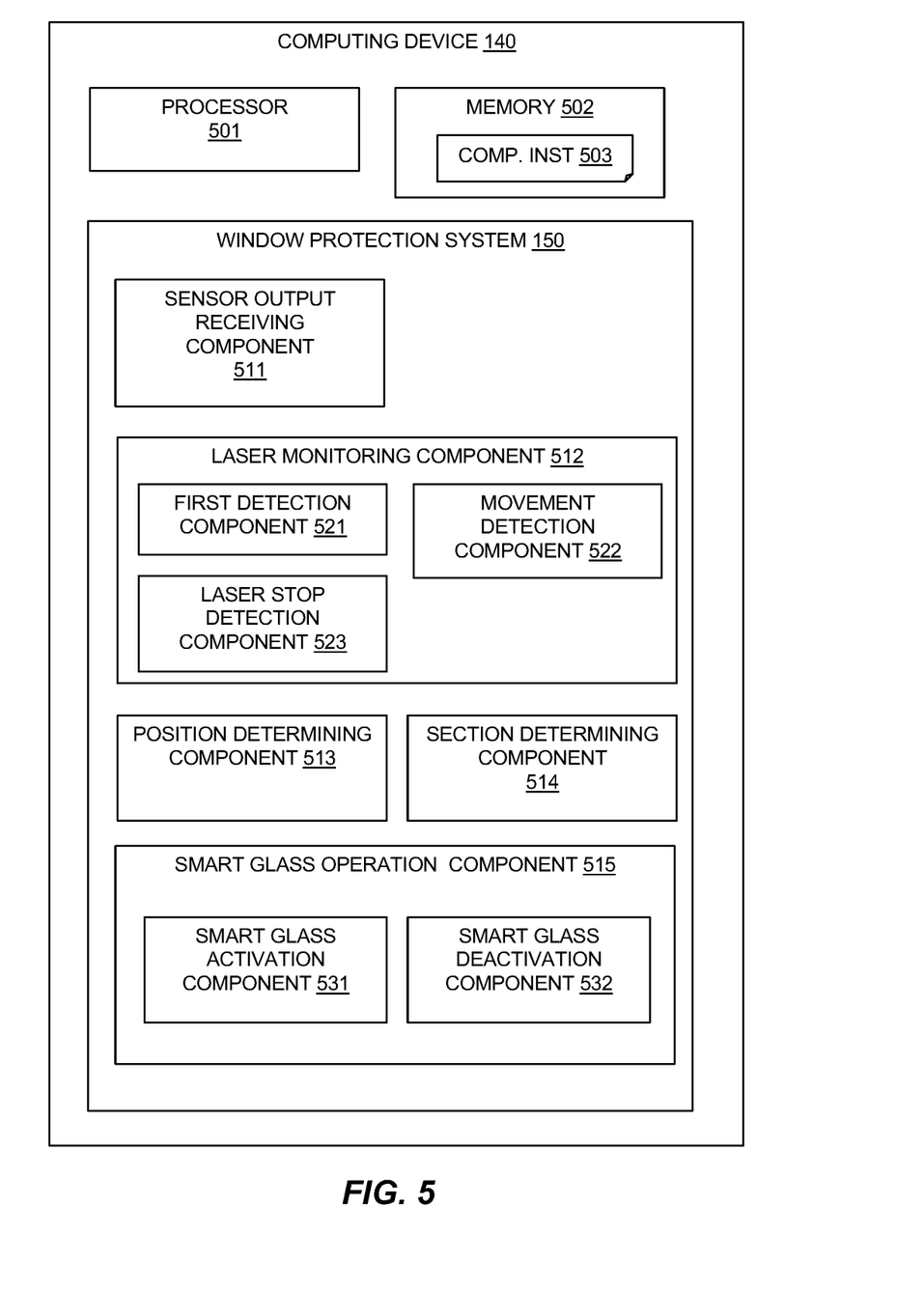
FIG. 5 is block diagram of an example embodiment of a system in accordance with the present invention.

Referring to FIG. 5, a block diagram shows further features of the window protection system 150.

A computing device 140 at which the window protection system 150 may be provided may include at least one processor 501, a hardware module, or a circuit for executing the functions of the described components which may be software units executing on the at least one processor. Multiple processors running parallel processing threads may be provided enabling parallel processing of some or all of the functions of the components. Memory 502 may be configured to provide computer instructions 503 to the at least one processor 501 to carry out the functionality of the components of the window protection system 150.

The window protection system 150 may include a sensor output receiving component 511 for receiving data from a sensor arrangement arranged to detect laser light impacting on a window and to provide data as to the position of the impact on the window.

The window protection system 150 may include a laser monitoring component 512 for receiving input regarding detection of a laser beam impacting the window. The laser monitoring component 512 may include a first detection component 521 for receiving data regarding a first detection of a laser beam impacting the window, a movement detection component 522 for detecting when the laser beam moves to a new position impacting the window, and a laser stop detection component 523 for detecting when a laser beam has stopped impacting the window. In one embodiment, the movement detection component 522 may track the movement of a laser beam impact on a window.

The window protection system 150 may include a position determining component 513 for determining the position of the laser beam impact on the window and a section determining component 514 for determining a section of the window to be activated.

The window protection system 150 may include a smart glass operation component 515 including a smart glass activation component 531 for controlling activation of the smart glass in sections of the window to make the section impenetrable to laser light and a smart glass deactivation component 532 for controlling deactivation of sections of the window.

Figure 6:
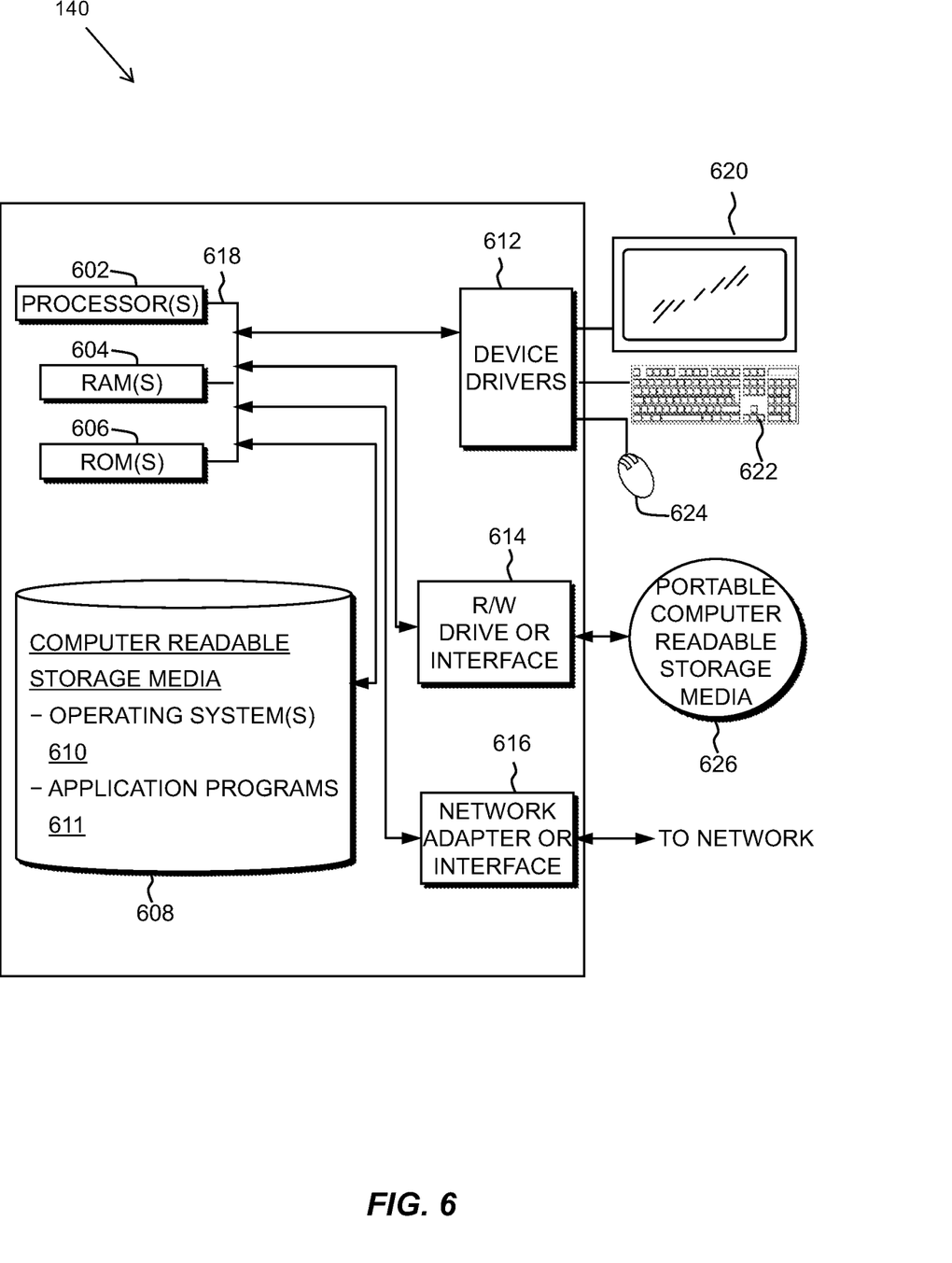
FIG. 6 is a block diagram of an embodiment of a computer system in which the present invention may be implemented.

FIG. 6 depicts a block diagram of components of the computing device 140 of the system 100 of FIG. 1, in accordance with an embodiment of the present invention. It should be appreciated that FIG. 6 provides only an illustration of one implementation and does not imply any limitations with regard to the environments in which different embodiments may be implemented. Many modifications to the depicted environment may be made.

Computing device 140 can include one or more processors 602, one or more computer-readable RAMs 604, one or more computer-readable ROMs 606, one or more computer readable storage media 608, device drivers 612, read/write drive or interface 614, and network adapter or interface 616, all interconnected over a communications fabric 618. Communications fabric 618 can be implemented with any architecture designed for passing data and/or control information between processors (such as microprocessors, communications and network processors, etc.), system memory, peripheral devices, and any other hardware components within the system.

One or more operating systems 610, and application programs 611, such as the window protection system 150 are stored on one or more of the computer readable storage media 608 for execution by one or more of the processors 602 via one or more of the respective RAMs 604 (which typically include cache memory). In the illustrated embodiment, each of the computer readable storage media 608 can be a magnetic disk storage device of an internal hard drive, CD-ROM, DVD, memory stick, magnetic tape, magnetic disk, optical disk, a semiconductor storage device such as RAM, ROM, EPROM, flash memory, or any other computer readable storage media that can store a computer program and digital information, in accordance with embodiments of the invention.

Computing device 140 can also include a R/W drive or interface 614 to read from and write to one or more portable computer readable storage media 626. Application programs 611 on computing device 140 can be stored on one or more of the portable computer readable storage media 626, read via the respective R/W drive or interface 614 and loaded into the respective computer readable storage media 608.

Computing device 140 can also include a network adapter or interface 616, such as a TCP/IP adapter card or wireless communication adapter. Application programs 611 on computing device 140 can be downloaded to the computing device from an external computer or external storage device via a network (for example, the Internet, a local area network or other wide area networks or wireless networks) and network adapter or interface 616. From the network adapter or interface 616, the programs may be loaded into the computer readable storage media 608. The network may comprise copper wires, optical fibers, wireless transmission, routers, firewalls, switches, gateway computers and edge servers.

Computing device 140 can also include a display screen 620, a keyboard or keypad 622, and a computer mouse or touchpad 624. Device drivers 612 interface to display screen 620 for imaging, to keyboard or keypad 622, to computer mouse or touchpad 624, and/or to display screen 620 for pressure sensing of alphanumeric character entry and user selections. The device drivers 612, R/W drive or interface 614, and network adapter or interface 616 can comprise hardware and software stored in computer readable storage media 608 and/or ROM 606.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Improvements and modifications can be made to the foregoing without departing from the scope of the present invention.

What is claimed is:

1. A computer-implemented method for smart window activation to prevent laser disturbance, comprising:
   detecting a laser beam impact on a window, wherein the window includes smart glass, and wherein the smart glass comprises micro-blind glass;
   determining a position of the laser beam impact on the window;
   determining a section of the window in which the smart glass is to be activated, wherein the section includes the position of the laser beam impact; and
   activating the smart glass in the section of the window; wherein the activating controls an applied voltage causing rolled micro-blinds to stretch out and block laser light.

2. The method of claim 1, further comprising:
   receiving input that the laser beam impact on the window has stopped; and
   deactivating the smart glass in the section of the window.

3. The method of claim 1, further comprising:
   receiving input from one or more sensors monitoring the window when the laser beam impact is detected, wherein the received input includes data relating to the position of the laser beam impact on the window.

4. The method of claim 1, wherein determining the position of the laser beam impact on the window comprises determining coordinates of the position in relation to a geometry of the window and to predefined sections of the smart glass.

5. The method of claim 1, wherein the section of the window is configured to be an area sufficiently large to prevent disturbance by the laser beam impact whilst minimizing restriction to viewing through the window.

6. The method of claim 1, wherein detecting the laser beam impact on the window comprises receiving data relating to sensed laser light transmitted within the window to sensors located at edges of the window, and wherein determining the position of the laser beam impact on the window analyzes the sensed laser light to determine the position of the laser beam impact.

7. The method of claim 1, wherein detecting the laser beam impact on the window comprises receiving data relating to laser light captured by a camera directed to the window, and wherein determining the position of the laser beam impact on the window analyzes the laser light captured by the camera to determine the position of the laser beam impact.

8. The method of claim 1, further comprising:
   determining movement of the laser beam impact on the window;
   determining a new position of the laser beam impact on the window;
   determining a new section of the window in which the smart glass is to be activated, wherein the new section includes the new position;
   activating the smart glass in the new section of the window;
   determining a previously activated section of the window in which the smart glass was previously activated; and
   deactivating the smart glass in the previously activated section of the window.

9. The method of claim 8, further comprising:
   tracking a laser beam impact on the window;
   in response to tracking the laser beam impact on the window, determining a path of the laser beam impact across the window, wherein the path comprises sections of the window; and
   activating the smart glass within the sections of the window in the path of the laser beam impact across the window.

10. A computer system for smart window activation to prevent laser disturbance, the computer system comprising:
    one or more processors, one or more computer-readable memories, one or more computer-readable tangible storage devices, and program instructions stored on at least one of the one or more computer-readable tangible storage devices for execution by at least one of the one or more processors via at least one of the one or more computer-readable memories, the program instructions comprising:
    program instructions to detect a laser beam impact on a window, wherein the window includes smart glass, and wherein the smart glass comprises micro-blind glass;
    program instructions to determine a position of the laser beam impact on the window;
    program instructions to determine a section of the window in which the smart glass is to be activated, wherein the section includes the position of the laser beam impact; and
    program instructions to activate the smart glass in the section of the window; wherein the activating controls an applied voltage causing rolled micro-blinds to stretch out and block laser light.

11. The computer system as claimed in claim 10, further comprising:
    program instructions to determine movement of the laser beam impact on the window;
    program instructions to determine a new position of the laser beam impact on the window;
    program instructions to determine a new section of the window in which the smart glass is to be activated, wherein the new section includes the new position;
    program instructions to activate the smart glass in the new section of the window;
    program instructions to determine a previously activated section of the window in which the smart glass was previously activated; and
    program instructions to deactivate the smart glass in the previously activated section of the window.

12. An apparatus for smart window activation, comprising:
    a window formed of smart glass capable of being activated in discrete sections to be impenetrable to laser light and having a smart glass activation system, wherein the smart glass comprises micro-blind glass;
    a sensor arrangement arranged to detect laser light impacting on the window and to provide data as to a position of the impact on the window;
    a computer-implemented window protection system, the computer-implemented window protection system comprising:
    one or more computer-readable tangible storage devices and program instructions stored on at least one of the one or more computer-readable tangible storage devices, the program instructions comprising:

program instructions to receive input regarding detecting a laser beam impact on the window from the sensor arrangement;

program instructions to determine a position of the laser beam impact on the window;

program instructions to determine a section of the window in which the smart glass is to be activated, wherein the section includes the position of the laser beam impact; and program instructions to activate the smart glass in the section of the window; wherein the activating controls an applied voltage causing rolled microblinds to stretch out and block laser light.

13. The apparatus of claim 12, wherein determining the position of the laser beam impact on the window comprises determining coordinates of the position in relation to a geometry of the window and to predefined sections of the smart glass.

14. The apparatus of claim 12, wherein the window is a windscreen of a vehicle.

15. The apparatus of claim 12, wherein the sensor arrangement includes sensors provided at least two edges of the window for detecting scattered light of the laser beam impact through the glass.

16. The apparatus of claim 15, wherein the sensor arrangement determines data as to the position of the laser beam impact on the window by detecting the scattered light at two or more edges of the window and analyzing the intensity of the scattered light at the two or more edges.

17. The apparatus of claim 12, wherein the sensor arrangement includes a camera monitoring the window.

18. The apparatus of claim 17, wherein the camera determines a location on the window of the laser beam impact.

* * * * *